(12) United States Patent
Lautenschlaeger

(10) Patent No.: US 10,925,553 B2
(45) Date of Patent: Feb. 23, 2021

(54) MEDICAL IMAGING APPARATUS

(71) Applicant: Siemens Healthcare GmbH, Erlangen (DE)

(72) Inventor: Stefan Lautenschlaeger, Nuremberg (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 16/702,802

(22) Filed: Dec. 4, 2019

(65) Prior Publication Data

US 2020/0187873 A1 Jun. 18, 2020

(30) Foreign Application Priority Data

Dec. 12, 2018 (EP) ..................................... 18211953

(51) Int. Cl.
  *A61B 6/00* (2006.01)
  *A61B 6/03* (2006.01)
  *A61B 6/02* (2006.01)
  *A61G 3/00* (2006.01)
  *A61B 6/04* (2006.01)

(52) U.S. Cl.
  CPC .............. *A61B 6/035* (2013.01); *A61B 6/025* (2013.01); *A61B 6/0487* (2020.08); *A61B 6/4452* (2013.01); *A61B 6/4476* (2013.01); *A61G 3/001* (2013.01)

(58) Field of Classification Search
  CPC .... A61G 3/001; A61G 2203/80; A61B 6/035; A61B 6/0487; A61B 6/025; A61B 6/4452; A61B 6/4476; A61B 6/4405; A61B 6/44; A61B 6/42
  See application file for complete search history.

(56) References Cited

U.S. PATENT DOCUMENTS

| | | | |
|---|---|---|---|
| 2012/0189102 A1 | 7/2012 | Maurer, Jr. et al. | |
| 2014/0064440 A1* | 3/2014 | Hara | A61B 6/508 378/4 |
| 2015/0065861 A1* | 3/2015 | Yamagata | G01T 1/1611 600/411 |
| 2016/0015343 A1* | 1/2016 | Fortuna | A61B 6/0407 378/51 |

(Continued)

FOREIGN PATENT DOCUMENTS

WO WO 2017180566 A2 10/2017

*Primary Examiner* — Kiho Kim
(74) *Attorney, Agent, or Firm* — Harness, Dickey & Pierce, P.L.C.

(57) ABSTRACT

A medical imaging apparatus for computer tomography, includes a first housing frame; a scanning section, movably disposed in an axial direction with respect to the first housing frame; and driving device(s). The scanning section includes an essentially toroidal scanning section housing including at least one uncovered axial surface, and a radiation source and a radiation detector, rotatably disposed inside of the essentially toroidal scanning section housing. The driving device(s) are configured to move the scanning section along an axial direction with respect to the first housing frame to perform a telescopic motion of the radiation source and radiation detector, during an operation of the medical imaging apparatus. The at least one uncovered axial surface of the essentially toroidal scanning section housing is movable along the axial direction.

23 Claims, 3 Drawing Sheets

(56) References Cited

U.S. PATENT DOCUMENTS

2017/0119322 A1* 5/2017 Yamada ................ A61B 6/032
2018/0249970 A1 9/2018 Nett et al.
2019/0357862 A1* 11/2019 Bailey .................... A61B 6/04

* cited by examiner

MEDICAL IMAGING APPARATUS

PRIORITY STATEMENT

The present application hereby claims priority under 35 U.S.C. § 119 to European patent application number EP 18211953.7 filed Dec. 12, 2018, the entire contents of each of which are hereby incorporated herein by reference.

FIELD

Embodiments of the invention generally relate to a medical imaging apparatus for computer tomography, comprising a scanning section, the scanning section comprising an essentially toroidal scanning section housing with at least one uncovered axial surface, and at least one radiation source and at least one radiation detector, each of which are disposed, rotably with respect to a rotation axis, inside of the scanning section housing, the rotation axis thereby defining an axial direction.

BACKGROUND

When treating a patient with a possible trauma or a stroke, typically the diagnosis is done by physician with the help of images. For a comprehensive understanding of the medical situation of a patient, the images are normally provided as a 3D volume model from a computer tomography (CT) of the affected area. This means that the medical imaging process consists of a series of single X-ray shots taken from different angles and a subsequent mathematical back-transformation to obtain the 3D model from the X-ray shots (e.g. via an inverse Radon transform from the inferred absorption with respect to each angle). From this 3D model, "slices" at different heights along an axis through the volume may be presented to the physician as series of images.

In order to perform the X-ray shots from different angles, a CT imaging apparatus comprises a toroidal housing in which an X-ray source and an X-ray detector are disposed rotably with respect to the toroid's symmetry axis and opposed to each other with respect to the toroid's inner hole, in which the patient is positioned for taking the X-ray shots. Both the X-ray source and the X-ray detector, while taking the individual X-ray images which are the basis data for the CT imaging process, move along the axis in order to cover a larger volume of the patient's body. Thus, there exists some sort of a lower bound on the dimensions of a CT imaging apparatus given by these restrictions.

For treating a severe trauma or a stroke, time is an important factor. The earlier the proper treatment starts, the higher are the possibilities of a full recovery without any lasting consequences. In case of a stroke, e.g., it may be crucial for the oxygen supply of certain brain regions that a thrombus causing the stroke gets removed as soon as possible. In order to start the proper treatment, a detailed diagnosis and, hence, images from the affected region of the body are required.

There exist CT imaging devices which are mounted in ambulances. However, these devices typically have several drawbacks: in case that they require their own table for positioning the patient, the device is rather large and can only be mounted in very long ambulance vehicles. Furthermore, the CT imaging devices are configured for a perfectly leveled ground (as it is the case in a hospital), but not for the use while driving over streets with possible slopes or even bumps. Therefore, the table needs to be leveled. This leads to additional costs for the whole CT medical imaging system, and furthermore to more weight to be moved in the ambulance.

SUMMARY

At least one embodiment of the invention presents a medical imaging apparatus which allows for performing a stable imaging process inside a medical vehicle, such as an ambulance, without the need of extensive changes to the vehicle itself.

According to at least one embodiment of the invention, a medical imaging apparatus for computer tomography, comprises a scanning section, at least a first housing frame and driving devices. The scanning section comprises an essentially toroidal scanning section housing with at least one uncovered axial surface, and at least one radiation source and at least one radiation detector, each of which are disposed, rotably with respect to a rotation axis, inside of the scanning section housing, the rotation axis thereby defining an axial direction. The scanning section is disposed movably in the axial direction with respect to the first housing frame, and the driving devices are configured to move the scanning section along the axial direction with respect to the first housing frame, in particular, during an operation of the medical imaging apparatus and/or during a preparation step for the operation, to perform a telescopic motion, such that the at least one uncovered axial surface of the scanning section housing is moved along the axial direction the at least one uncovered axial surface of the scanning section housing is moved along the axial direction, and at least a part of an axial motion of the at least one radiation source and the at least one radiation detector during an operation of the medical imaging apparatus is provided by the telescopic motion.

Another aspect of at least one embodiment of the invention is given by the use of a medical imaging apparatus as described above in at least one embodiment, in combination with a mobile, preferably fixable stretcher for positioning a patient. Thereby, preferably a medical imaging process is performed by the medical imaging apparatus, while the patient on which the imaging process shall be performed is positioned on the mobile stretcher. The mobile stretcher may be fixed by fixing device(s) such as brakes inherent to the stretcher for the imaging process. The features, advantages and characteristics of the medical imaging device and of its preferred embodiments may be extended to its use in combination with a mobile stretcher in a straight forward manner.

Yet another aspect of at least one embodiment of the invention is given by a vehicle, in particular an ambulance, comprising at least one embodiment of a medical imaging apparatus as described above. The features, advantages and characteristics of the medical imaging device and of its preferred embodiments may be extended to the vehicle in a straight forward manner.

BRIEF DESCRIPTION OF THE DRAWINGS

The attributes and properties as well as the advantages of the invention which have been described above are now illustrated with help of a drawing of an embodiment example. In detail, FIG. 1 schematically shows a cross-section through a medical imaging apparatus for computer tomography with a scanning section mounted on two telescopically movable housing frames, FIG. 2 schematically shows a cross-section of a different embodiment of a medical apparatus with a scanning section mounted on telescope rings for its axial motion, and FIG. 3 schematically shows a side view of yet another embodiment of a medical imaging apparatus mounted inside an ambulance and used together with an ambulance stretcher.

Parts and variables corresponding to one another are provided with in each case the same reference numerals in all figures.

DETAILED DESCRIPTION OF THE EXAMPLE EMBODIMENTS

Figure 1:
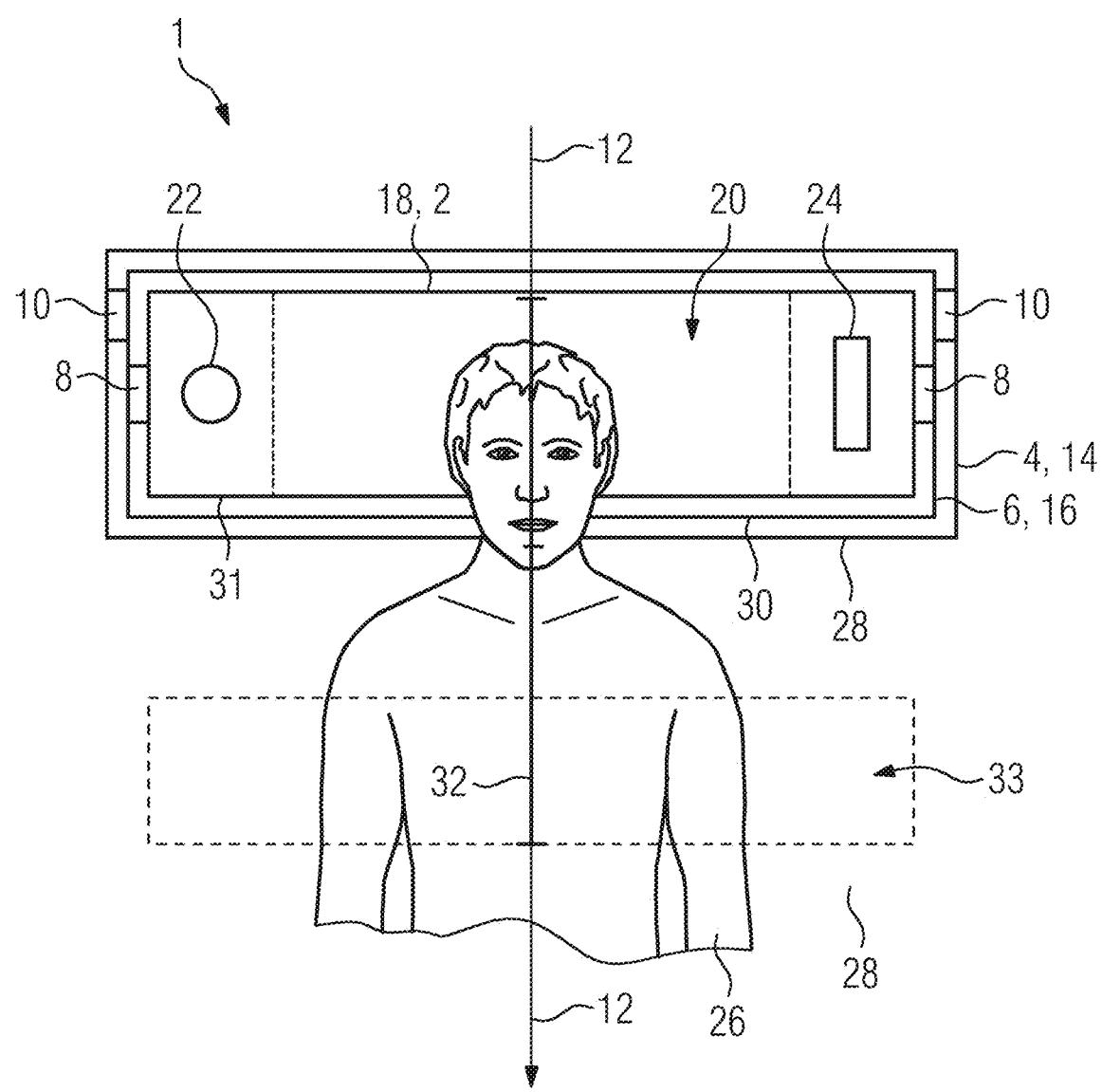

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

According to at least one embodiment of the invention, a medical imaging apparatus for computer tomography, comprises a scanning section, at least a first housing frame and driving devices. The scanning section comprises an essentially toroidal scanning section housing with at least one uncovered axial surface, and at least one radiation source and at least one radiation detector, each of which are disposed, rotably with respect to a rotation axis, inside of the scanning section housing, the rotation axis thereby defining an axial direction. The scanning section is disposed movably in the axial direction with respect to the first housing frame, and the driving devices are configured to move the scanning section along the axial direction with respect to the first housing frame, in particular, during an operation of the medical imaging apparatus and/or during a preparation step for the operation, to perform a telescopic motion, such that the at least one uncovered axial surface of the scanning section housing is moved along the axial direction the at least one uncovered axial surface of the scanning section housing is moved along the axial direction, and at least a part of an axial motion of the at least one radiation source and the at least one radiation detector during an operation of the medical imaging apparatus is provided by the telescopic motion.

Embodiments which show particular advantages and may be inventive in their own respect are given by the dependent claims as well as in the subsequent description.

The notion of computer tomography shall in particular comprise an imaging process for which a plurality of X-Ray shots is taken with varying angles of view, each of the X-Ray shots, representing an absorption distribution for X-race with a beam path corresponding to each angle of view, and a 3D-model of a body part is reconstructed from the X-Ray imaging data, preferably allowing for a distinguishable resolution of different kinds of tissue of the body part. In this sense, the medical imaging apparatus is in particular configured to perform at least the X-Ray imaging parts of the described process, this means, taking a sufficiently large set of X-Ray shots to a sufficiently large set of different angles of view. Preferably, the medical imaging apparatus also comprises device(s) to perform the transformations on the X-Ray images required for reconstructing the 3D-model of the analyzed body part, and/or cross-sectional views of such a model.

Preferably, the scanning section is configured to perform a full scan of X-Ray images, defining thereby the angle of view in circumferential direction along a full closed circle. Most preferably, the scanning section, to this end, comprises all the devices necessary for the scan, such as rotational drives for driving the radiation source or sources, and for deriving the radiation detector or detectors involved, as well as power supply device(s) and/or power conversion device(s) for providing a power supply to the radiation source and detector, and data pre-processing device(s) for processing the generated X-Ray images into a data stream appropriate for transmission.

In particular, and according to the specific embodiment of the imaging process (defined by the mathematical transformation used for reconstructing the 3D-model from the X-Ray images, as well as the number of X-Ray images taken at a time), the scanning section may comprise more than one radiation source and/or more than one radiation detector. Preferably, all radiation sources and all radiation detectors are comprised in the scanning section. For providing different angles of view, the or each radiation source and the or each radiation detector is disposed on a rotary frame in the scanning section, the rotary frame being mounted on respective bearings, allowing for a rotational movement of the rotary frame, and being mechanically coupled to at least one rotational drive for providing the rotational movement. Preferably, the or each radiation source and the or each radiation detector are mounted on one single rotary frame, however, embodiments with separate rotary frames for a radiation source and for a radiation detector are conceivable.

The notion of an essentially toroidal scanning section housing shall in particular comprise a housing that is given, as a first approximation, by a surface of revolution, wherein the generating curve from which by rotating, the surface of revolution may be obtained, forms a closed loop, and in particular may be quadratic, rectangular, or trapezoidal, and may in general also comprise rounded corners. In particular, the scanning section housing has an inner surface given by an inner ring section enclosing a hole for at least partially positioning the body part to be analyzed by the medical imaging apparatus during its operation. In this respect, the essentially toroidal form of the scanning section housing may show slight deviations from the ideal surface of revolution, for example by forming grab handles and/or flattening out a section of the inner ring and/or forming device(s) for guiding along a stretcher, and the like. Preferably, the rotation axis for the at least one radiation source and the at least one radiation detector also forms the rotation axis for the surface of revolution from which the scanning section housing is given, at least as a first approximation.

The notion of the at least one uncovered axial surface of the scanning section housing shall comprise that for the scanning section housing, which is limited in axial direction by two surfaces, and which may show some limited curvature and/or roundings in the axial direction, at least one of these two axial surfaces is uncovered with respect to an overall accessibility. This means, that during a movement of the scanning section housing in axial direction, the at least one uncovered axial surface also gets moved along the axial direction, such that the accessible space in the intermediate proximity of the uncovered axial surface gets changed.

In particular, the at least first housing frame may be mechanically connected to a base frame of the medical imaging apparatus which fixes a reference position such that the telescopic motion leads to a linear movement of the scanning section with respect to that base frame. In particular, the driving device(s) for providing the axial motion may form part of the first housing frame.

Preferably, the first housing frame comprises a cylindrical ring that is compatible with an outer surface of the scanning section housing in a sense that when performing the telescopic motion in a way that the axial length of an ensemble formed by the scanning section housing and the first housing frame increases, the radial steps on the outer surface of this ensemble along the axial direction are negligible compared to the overall diameter of the ensemble. At least one part of the housing frame and the scanning section housing may comprise a set of guide rails or similar elements in each of which an axially movable bar mechanically fixed to the other part is guided in order to provide the telescopic motion of the at least the two mentioned parts, i.e., the first housing section and the scanning section housing, relative to each other. In case the first housing frame comprises a first housing ring, the first housing ring may be shaped accordingly to an outer surface of the scanning section housing. The telescopic motion of the first housing ring with respect to the outer surface of the scanning section housing, and possibly with respect to further housing rings may be to by the form of the housing rings only. In this case, the driving device(s) may be given by one linear driving device(s) or a set of linear driving device(s) configured to move the scanning section housing against a base frame or a back wall of the medical imaging apparatus.

The first housing frame, as an alternative, may be given by a set of guide rails and/or corresponding bars, without any cylindrical ring. In this case, the first housing frame may essentially of the linear bearing components required to provide for an axial movement of the scanning section with respect to the base frame of the medical imaging apparatus which are not mechanically fixed to the scanning section housing.

Typically, a medical imaging apparatus for computer tomography as known in the art comprises rotary and linear motion drives and frames within one overall housing, often called a gantry. As normally such a computer tomography apparatus shall be capable of generating a 3D-model of at least parts of a thorax of a person, this puts a lower bound on the diameter of an inner hole of the gantry as well as on its axial length. In a hospital environment, the axial movement may be provided by an axially movable support on which a patient may lay down during the imaging process. However, for mobile units to be used in ambulances, a unit of a medical imaging apparatus also comprising a special support for fitting one entire person would be too large and too heavy. However, providing the axial movement of the scanning components for the X-Ray imaging process by specific driving device(s) and frames within a housing would also lead to a housing with an axial length that is not desirable, as normally, a computer tomography scan for detecting trauma goes from the head of a patient at least to his heart, spanning up to 50 cm or even more.

This space problem is solved according to at least one embodiment of the invention by enclosing all the components required for an X-Ray image shot into the scanning section, which may be constructed much narrower. The linear movement is then provided by the linear driving device(s) and by the first housing frame which during the linear movement acts as a support for the scanning section, thus leading to the telescopic motion. So the different angles of view necessary for the imaging process are, on the one hand, provided by the rotation of the X-Ray components inside the scanning section, leading to different angles with respect to the rotation axis, and on the other hand, by the linear movement of the scanning section in the axial direction. Essentially, the scanning section is shifted over the body parts to be scanned and analyzed by telescopic motion, with no need for a common housing enclosing all of the scanning section and the first housing frame and/or its linear bearings, thus allowing for a far more compact construction of the medical imaging apparatus.

Preferably, in a base position, the scanning section and the first housing frame form an ensemble, wherein an axial length of the ensemble is given by the maximum of an axial length of the scanning section and an axial length of the first housing frame. In particular, this means that there exists a configuration in which the "telescope" given by the scanning section and the first housing section is the shortest possible with respect to its axial length, i.e., the "telescope" is maximally pulled back. While the medical imaging apparatus is not in operation, this base position may be used for a compact storage. As the scanning section may be constructed with an axial length of typically as low as 25-30 cm, possibly even less, and a development for compactifying components even further, which could lead to axial lengths in the range of 15-20 cm, the length of the ensemble in the base position is of a similar order, which makes the medical imaging apparatus particularly suited for use in an ambulance where space is an important issue.

In an embodiment, the first housing frame comprises a first housing ring which encompasses the at least one radiation source and the at least one radiation detector of the scanning section for at least one position of the telescopic motion. This means that for all possible axial configurations of the ensemble formed by the scanning section and the first housing frame, there exists at least one such configuration—equivalent to a specific position of the telescopic motion—in which the first housing ring of the first housing frame encompasses the radiation source and detector, and thus, essentially encompasses the scanning section, at least its largest part. In particular, this may lead to a true "telescope" of the first housing ring and the scanning section housing, forming an essentially closed outer surface. The first housing ring has a shielding an protection effect during the axial motion of the scanning section such that no part of a human body nor any other object can get into the pathway of the scanning section's axial movement. This protects both the technical integrity of the medical imaging device and the patient to be analyzed, as well as the medical staff in the immediate surroundings of the medical imaging device.

Preferably, the first housing frame in a direction perpendicular to the axial direction shows a cross-section essentially congruent to an outer surface of the scanning section housing, and in particular, the first housing frame and the outer surface of the scanning section housing are essentially cylindrical.

In an embodiment, the first housing frame encompasses the scanning section in the base position. This means that during the telescopic motion, the scanning section housing slides inside of the first housing ring. This is particularly easy to construct as for the telescopic motion, there are no restrictions on the delicate scanning section, and all the necessary component for the axial movements may be disposed on the outside of the scanning section housing and in the inside of the first housing ring.

In an alternative embodiment, the first housing frame is run into an annular grove of the scanning section housing in the base position. This embodiment allows for a particularly compact construction, if space restrictions on the application site are a very important issue.

In an embodiment, the medical imaging apparatus further comprises a second housing frame, wherein the scanning section, the first housing frame and the second housing frame are disposed movably in the axial direction with respect each other, and wherein the driving device(s) are configured to move the scanning section along the axial direction with respect to the first housing frame and with respect to the second housing frame to perform the telescopic motion. In particular, the second housing frame geometrically corresponds to the first housing frame in a sense that in case the first housing frame comprises a first housing ring, the second housing frame comprises a second housing ring, such that an ensemble of the scanning section, the first housing frame and the second housing frame for the telescopic motion forms a true "telescope" with an essentially closed outer surface. In this case, driving device(s) for the telescopic motion may be one linear drive or a set of linear drives configured to move the scanning section housing relative to a base frame or a back wall of the medical imaging apparatus.

If the first housing frame is essentially given by a set of guide rails and/or linear bearings, then preferably also the second housing frame is given by a corresponding set of guide rails, and/or guiding elements and/or linear bearings. A second housing frame allows for a longer axial extension of the telescopic motion, and thus, for scanning a larger area with the scanning section. To this end, in particular, there may exist further housing frames, preferably of similar shape than the first and second housing frame.

In an embodiment, the medical imaging apparatus further comprises an outer housing ring, the outer housing ring encompassing the scanning section and the first housing frame and, if it applies, all further housing frames, and extending in one axial direction at least to an outermost axial extension of the scanning section in the telescopic motion. In particular, this means that due to the telescopic motion, the possible axial positions of the scanning section define a span for the scanning section, and the outer housing ring extends at least to one end of this span, which may be given by a back wall of the medical imaging apparatus. Preferably, the outer housing ring extends to the outermost axial extension of the scanning section in a base position where the "telescope" is pulled back. The outer housing ring then further protects the scanning section and the first housing frame while the medical imaging apparatus is not in use. Preferably, to this end an axial length of the outer housing ring at least exceeds the axial length of the scanning section housing.

Preferably, the driving devices comprises at least one linear driving devices mounted on a mount support mechanically connected with a base frame or a back wall of the medical imaging apparatus, and wherein the linear driving device(s) is configured to drive the scanning section housing in an axial direction relative to the mount support. This in particular comprises the case that the first housing frame, and, if applicable, any further housing frames, do not comprise their own active driving device(s). The axial motion of the scanning section is then provided by a linear drive, comprising e.g. a spindle or a shaft, which is mounted on the mount support that in turn is mechanically connected and in particular fixed to the base frame or to a back wall. This allows for omitting any linear guide rails in the first housing frame (and in possible further housing frames), as they are not needed for driving, and thus, the "telescope" can be formed as a true telescopic shape with an essentially closed outer surface in the position of its largest axial extension.

Preferably, the driving device(s) are configured to provide an axial motion of the scanning section spanning at least 20 cm, more preferably of at least 30 cm, furthermore preferably of at least 35 cm, most preferably of at least 40 cm, wherein an inner bore of the scanning section housing is at least 30 cm, preferably at least 35 cm. The notion of a span of the axial motion of the scanning section in particular shall comprise the overall axial length that is covered by the scanning section during the axial motion, counting in also the scanning section housing's own length. Furthermore preferably, the first housing frame and possibly further housing frames is/are also configured to support and allow for the axial span of at least 35 cm. The given values allow for a use of the medical imaging apparatus for imaging a patient's head and thus, for detecting a stroke, such that the medical imaging apparatus may be used in an ambulance configured as a mobile stroke unit. To this end, in particular, the axial span is at most 75 cm, preferably at most 65 cm, and the inner bore of the scanning section housing is at most 60 cm, preferably at most 50 cm.

Preferably, the driving devices are configured to provide an axial motion of the scanning section spanning at least 65 cm, wherein the inner bore of the scanning section housing is at least 65 cm. Furthermore preferably, the first housing frame and possibly further housing frames is/are also configured to support and allow for the axial span of at least 65 cm. Most preferably, the medical imaging apparatus comprises a number of housing frames with an essentially equal axial length, which corresponds to the axial length L of the scanning section housing, such that the number of housing frames is 65 cm/L. With the given dimensions, the medical imaging apparatus allows for a scan of a human body from the head at least down to the heart, and thus, enables the use of the medical imaging devices in an ambulance configured as mobile unit for scanning the head and the hearth, or as a mobile trauma unit.

In an embodiment, the medical imaging apparatus further comprises a positioning board which is mechanically connected to a base frame of the medical imaging device and configured to be disposed essentially horizontally, and which is further configured to support a patient's head and/or a shoulder part of a patient's torso during operation of the medical imaging apparatus. Preferably, the positioning consists of a set of foldably connected rigid portions, and/or is mounted on an adjustable support. The rigid portions then may be folded into a storage configuration or a usage configuration, wherein in the usage configuration all rigid portions may essentially span a plane or a holder for the patients head and/or shoulders, and in the storage configuration, the rigid portions may be folded onto each other. The adjustable support may connect the positioning board with the base frame of the medical imaging apparatus in such a way that the positioning board may be positioned to support a patients head and/or shoulder parts when an imaging process is performed, while by way of the adjustable support the positioning board may be stored in a compact way when no imaging process is performed. While the medical imaging apparatus can be in principal operated with a patient laying on a mobile stretcher such as an ambulance stretcher, the positioning board helps to keep the body parts to be displayed by the medical imaging process in the right position for the X-Ray shots.

Preferably, the medical imaging apparatus further comprises moving device(s) configured to move, in particular automatically, a body transfer board with a patient into a determined position for performing a medical imaging process. A patient that is being transported on a stretcher, does not lie directly on the stretcher itself; rather, the patient lies on a body transfer board which gets transported by the stretcher. Such a body transfer board is used especially in situations in which the patient will probably be moved several times at an emergency ward or the like for analysis and treatment.

The moving device(s) may comprise a set of grippers each of which configured to grab a corresponding handle of the body transfer board. With the moving device(s), there is no need for a physically strong staff for moving the patient into an adequate position for the operation of the medical imaging apparatus. Furthermore, the moving device(s) may be configured to position a body transfer board into an optimal position for the medical imaging process.

In an embodiment, the medical imaging apparatus further comprises at least one wheel rotably mounted on an axis for moving the medical imaging apparatus. In particular, the medical imaging apparatus may comprise at least one, preferably two pairs of wheels, such that the medical imaging apparatus can be easily put aside when not in use. Preferably, each wheel may be fixed by fixing device(s) such as brakes.

Another aspect of at least one embodiment of the invention is given by the use of a medical imaging apparatus as described above in at least one embodiment, in combination with a mobile, preferably fixable stretcher for positioning a patient. Thereby, preferably a medical imaging process is performed by the medical imaging apparatus, while the patient on which the imaging process shall be performed is positioned on the mobile stretcher. The mobile stretcher may be fixed by fixing device(s) such as brakes inherent to the stretcher for the imaging process. The features, advantages and characteristics of the medical imaging device and of its preferred embodiments may be extended to its use in combination with a mobile stretcher in a straight forward manner.

In particular, the medical imaging device may be disposed in an ambulance, and the stretcher may form part of the equipment of the ambulance. Thus, the medical imaging process of a patient does not require any further horizontal board to be mounted at the medical imaging apparatus, but can be performed with the stretcher anyway present during the operation of the ambulance.

Yet another aspect of at least one embodiment of the invention is given by a vehicle, in particular an ambulance, comprising at least one embodiment of a medical imaging apparatus as described above. The features, advantages and characteristics of the medical imaging device and of its preferred embodiments may be extended to the vehicle in a straight forward manner.

FIG. 1 shows a longitudinal cross-section through a medical imaging apparatus 1 for computer tomography. The medical imaging apparatus 1 comprises a scanning section 2, a first housing frame 4 and a second housing frame 6. The medical imaging apparatus 1 further comprises driving device(s) 8 configured to provide for an axial motion of the scanning section 2 with respect to the second housing frame 6, and driving device(s) 10 for providing an axial motion of the second housing frame 6 with respect to the first housing frame 4. The driving device(s) 8 and the driving device(s) 10 are only schematically indicated in FIG. 1, and may be given by any sort of linear drive or motor capable of and configured to provide the respective axial motion. The axial motion is defined with respect to an axis 12.

The first housing frame 4 comprises a first housing ring 14 which has a cylindrical shape and is essentially rotationally symmetric with respect to the axis 12. The second housing frame 6 comprises a second housing ring 16 which is essentially cylindrically shaped and rotationally symmetric to the axis 12. The scanning section 2 comprises a scanning section housing 18, which has an essentially toroidal shape, and thus surrounds an inner bore 20 whose radial limits are indicated by the dashed lines. The scanning section 2 further comprises a radiation source 22 given by an X-Ray source for computed tomography, and a radiation detector 24 given by an X-Ray detector ensemble suitable for computed tomography. The radiation source 22 and the radiation detector 24 are disposed inside the scanning section housing 18 in a way that X-Ray radiation emitted from the radiation source 22 propagates through the inner bore 20 prior to impinging on the radiation detector 24. During an imaging process, both the radiation source 22 and the radiation detector 24 rotate about the axis 12, for which they may be disposed inside the scanning section housing 18 on a rotary frame not displayed in FIG. 1.

For the medical imaging process of the medical imaging apparatus 1, X-Ray shots from different angles of view are necessary. While the rotation of the radiation source 22 and the radiation detector 24 around the axis 12 may provide different angles of view in a plane perpendicular to the axis 12, for scanning larger objects or, more generally, body parts, a variation of such a plane perpendicular to the axis 12 is required. To this end, the radiation source 22 and the radiation detector 24 are moved along the axial direction defined by the axis 12. In the medical imaging apparatus 1, this is achieved by an axial motion of the scanning section 2 with respect to a patient 26. This axial motion is implemented by a telescopic motion of the scanning section 2, the first housing frame 4, and the second housing frame 6 relative to each other. The driving device(s) 10 thus move the second housing frame 6 inside the first housing frame 4 towards the lower end 28 of the first housing frame 4, while the driving device(s) 8 move the scanning section 2 inside the second housing frame 6 towards its lower end 30, such that the lower uncovered axial surface 31 of the scanning section housing 18 moves downwards with respect to the patient 26, until the scanning section 2 reaches a outer-most position 33 indicated by a dotted line.

Furthermore, inside of the scanning section housing 18, linear driving device(s) may be disposed to provide for an axial motion of both the radiation source 22 and the radiation detector 24 inside the scanning section housing 18. For the sake of simplicity, such additional driving device(s) are omitted in FIG. 1. By way of the described axial motion of the scanning section 2, the radiation source 22 and the radiation detector 24 may perform X-Ray shots in any plane perpendicular to the axis 12 along an axial imaging span 32. Preferably, for a mobile trauma unit, this axial span 32 is at least 60 cm, and the diameter of the inner for 20 of the scanning section housing 18 is at least 65 cm.

Figure 2:
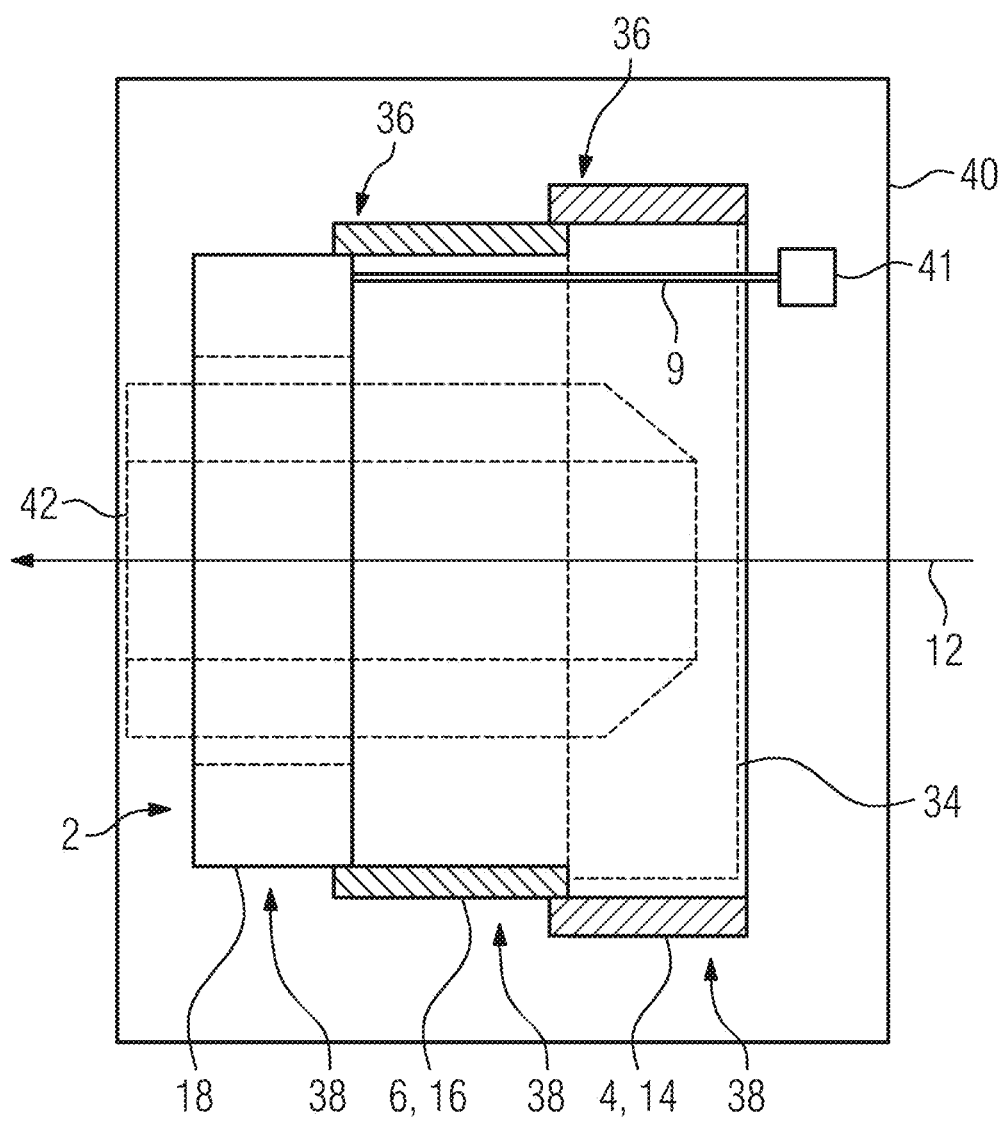

FIG. 2 shows a schematic longitudinal cross-section of a different embodiment of the medical imaging device 1. Here, the axial length of the first housing ring 14 (shaded) of the first housing frame 4, the axial length of the second housing ring 16 (shaded) of the second housing frame 6 and the axial length of the scanning section housing 18 are somewhat comparable to each other, such that when the scanning section 2 is moved along the axis 12 left-wards from a base position (indicated by dotted lines) to its leftmost extension, the first housing ring 14, the second housing ring 16 and the scanning section housing 18 form a true telescope with the respective radial steps 36 due to the radial thickness of the first housing ring 14 and the second housing ring 16 (which are not shown to scale, but are enlarged for illustration purposes). The ensemble 38 of the first and second housing frame 4, 6, and the scanning section 2 is mounted on a base frame 40 of the medical imaging apparatus 1. In order to position a patient properly for the medical imaging process, a furthermore positioning board 42 is disposed on the base frame 40 (dashed line). The scanning section housing is moved in the axial direction 12 by a linear drive 9 which is mounted on a mount support 41 fixed on the base frame 40. As an alternative, the mount support may be fixed to a back wall (not shown in FIG. 2) of the medical imaging apparatus 1.

Figure 3:
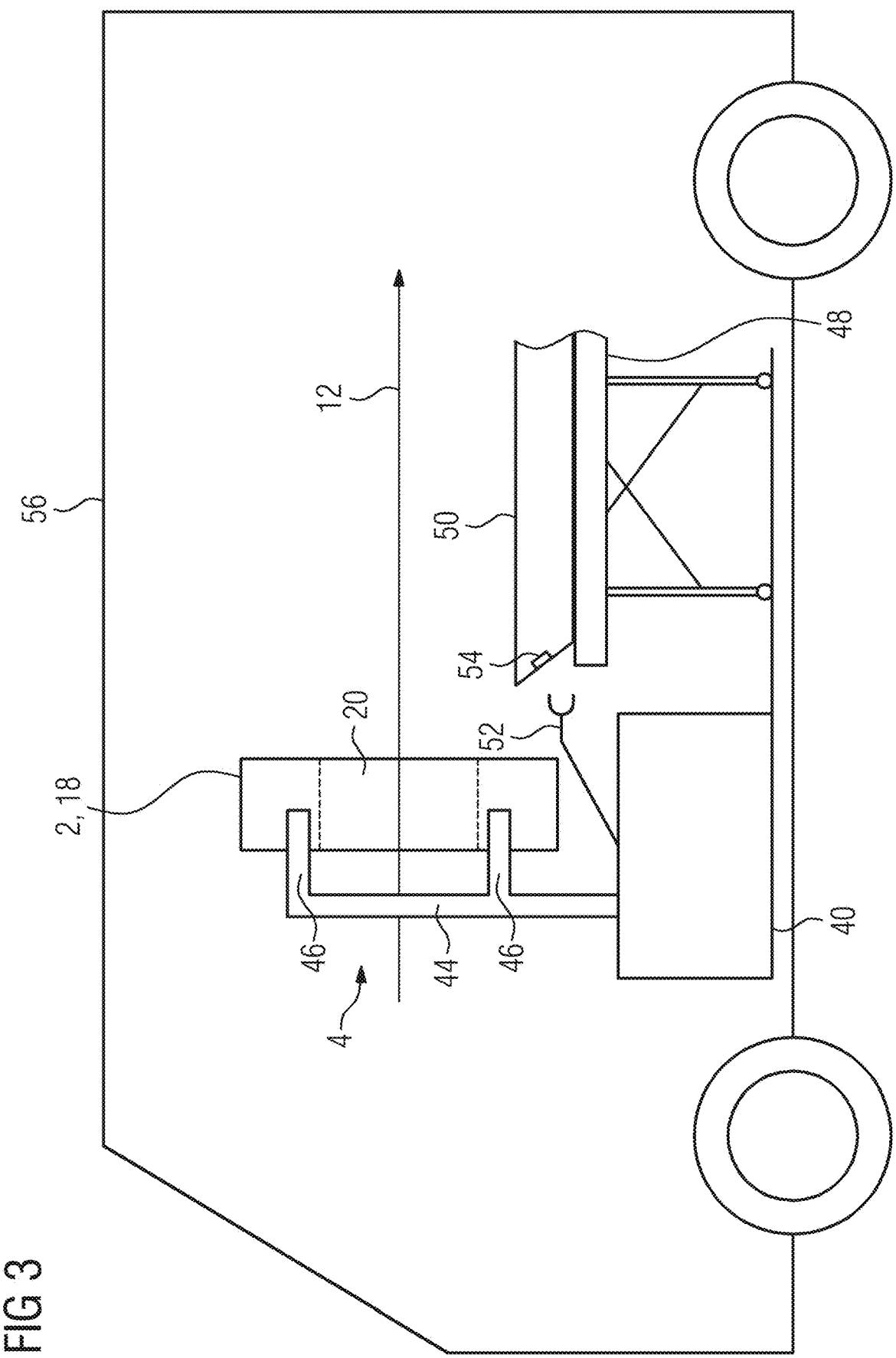

FIG. 3 shows a schematic side view of yet another embodiment of the medical imaging apparatus 1. The first housing frame 4 is given by a set of bars 44 and a set of guide rails 46. In the present embodiment, no first housing ring is used. The scanning section 2 is configured to move along the guide rails 46 by way of respective linear drives not displayed in FIG. 3 along the axis 12. The inner bore 20 of the scanning section housing 18 has a diameter of 30 cm and an axial span 32 of 35 cm, being sufficient for scanning a patient's head in order to analyze for a possible stroke of the patient. For the imaging process, the patient may be disposed on a stretcher 48 that may be rolled towards the base frame 40 and fixed either by breaks or by device(s) disposed on the base frame 40 (not displayed in FIG. 3). The patient furthermore may lay on a body transfer board 50 disposed on the stretcher 48, while moving device(s) 52 given by grippings mounted on the base frame 40 may position the body transfer board 50 into the proper position for the medical imaging process by grabbing respective handles 54 on the body transfer board 50. Finally, the medical imaging apparatus 1 may be disposed in a vehicle 56, which in the present case is given by an ambulance.

It has to be stated that the feature combinations of the embodiments shown in FIG. 1, FIG. 2, and FIG. 3 may also be interchanged in a sense that, for example, the medical imaging apparatus 1 of FIG. 1 may be used in combination with the stretcher 48 of FIG. 3 and/or inside the ambulance of FIG. 3. Furthermore, also the embodiment of the medical imaging apparatus 1 in FIG. 1 may comprise, for example, a positioning board 42 as shown in FIG. 2. Likewise, the dimensions for the diameter of the inner bore 20 and the axial span 32 of the shown embodiments is not necessarily linked to the specific embodiment.

Even though the invention has been illustrated and described in detail with help of a preferred embodiment example, the invention is not restricted by this example. Other variations can be derived by a person skilled in the art without leaving the extent of protection of this invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A medical imaging apparatus for computer tomography, comprising a scanning section; a first housing frame and a plurality of driving devices, the scanning section comprising:
   an essentially toroidal scanning section housing including at least one uncovered axial surface, and
   at least one radiation source and at least one radiation detector, each disposed, rotatably with respect to a rotation axis, inside of the essentially toroidal scanning section housing, the rotation axis defining an axial direction,
   wherein the scanning section is disposed movably in the axial direction with respect to the first housing frame, and
   wherein the plurality of driving devices are configured to move the scanning section along the axial direction with respect to the first housing frame to perform a telescopic motion, wherein:
      the at least one uncovered axial surface of the scanning section housing is movable along the axial direction, and
      at least a part of an axial motion of the at least one radiation source and the at least one radiation detector, during an operation of the medical imaging apparatus, is provided by the telescopic motion.

2. The medical imaging apparatus of claim 1, wherein in a base position, the scanning section and the first housing frame form an ensemble, an axial length of the ensemble being given by a maximum of an axial length of the scanning section and an axial length of the first housing frame.

3. The medical imaging apparatus of claim 2, wherein the first housing frame includes a first housing ring encompassing the at least one radiation source and the at least one radiation detector of the scanning section, for at least one position of the telescopic motion.

4. The medical imaging apparatus of claim 3, wherein in the base position, the first housing frame encompasses the scanning section.

5. The medical imaging apparatus of claim 3, wherein in the base position, the first housing frame is run into an annular grove of the scanning section housing.

6. The medical imaging apparatus of claim 3, further comprising an outer housing ring, the outer housing ring encompassing the scanning section and the first housing frame and extending in one axial direction at least to an outermost axial extension of the scanning section in the telescopic motion.

7. The medical imaging apparatus of claim 1, further comprising a second housing frame, wherein the scanning section, the first housing frame and the second housing frame are disposed movably in the axial direction with respect each other, and wherein the plurality of driving devices are configured to move the scanning section along the axial direction with respect to the first housing frame and with respect to the second housing frame, to perform the telescopic motion.

8. The medical imaging apparatus of claim 1, further comprising an outer housing ring, the outer housing ring encompassing the scanning section and the first housing frame and extending in one axial direction at least to an outermost axial extension of the scanning section in the telescopic motion.

9. The medical imaging apparatus of claim 1, wherein the plurality of driving devices comprises
   at least one linear driving device mounted on a mount support, mechanically connected with a base frame or a back wall of the medical imaging apparatus, the at least one linear driving device being configured to drive the scanning section housing in an axial direction relative to the mount support.

10. The medical imaging apparatus of claim 1, wherein the plurality of driving devices are configured to provide an axial motion of the scanning section over an axial span of at least 20 cm, and wherein an inner bore of the scanning section housing is at least 30 cm.

11. The medical imaging apparatus of claim 10, wherein the plurality of driving devices are configured to provide an axial motion of the scanning section over an axial span of at least 65 cm, and wherein the inner bore of the scanning section housing is at least 65 cm.

12. The medical imaging apparatus of claim 1, further comprising a positioning board mechanically connected to a base frame of the medical imaging apparatus, configured to be disposed essentially horizontally and further configured to support at least one of a head of a patient and a shoulder part of a torso of the patient, during operation of the medical imaging apparatus.

13. The medical imaging apparatus of claim 1, further comprising at least one moving device, configured to move a body transfer board for a patient into a determined position for performing a medical imaging process.

14. The medical imaging apparatus of claim 13, wherein the first housing frame includes a first housing ring encompassing the at least one radiation source and the at least one radiation detector of the scanning section, for at least one position of the telescopic motion.

15. The medical imaging apparatus of claim 1, further comprising
   at least one wheel rotatably mounted on an axis to move the medical imaging apparatus.

16. An arrangement, comprising:
   the medical imaging apparatus of claim 1; and
   a mobile stretcher for positioning a patient.

17. A vehicle, comprising the medical imaging apparatus of claim 1.

18. A medical imaging apparatus for computer tomography, comprising:
   a first housing frame;
   a scanning section, movably disposed in an axial direction with respect to the first housing frame and including
      an essentially toroidal scanning section housing including at least one uncovered axial surface, and
      at least one radiation source and at least one radiation detector, rotatably disposed inside of the essentially toroidal scanning section housing; and
   at least one driving device to move the scanning section along an axial direction with respect to the first housing frame to perform a telescopic motion of the at least one radiation source and the at least one radiation detector, during an operation of the medical imaging apparatus, the at least one uncovered axial surface of the essentially toroidal scanning section housing being movable along the axial direction.

19. The medical imaging apparatus of claim 18, wherein the first housing frame includes a first housing ring encompassing the at least one radiation source and the at least one radiation detector of the scanning section, for at least one position of the telescopic motion.

20. The medical imaging apparatus of claim 18, further comprising a second housing frame, wherein the scanning section, the first housing frame and the second housing frame are disposed movably in the axial direction with respect each other, and wherein the at least one driving device includes a plurality of driving devices, configured to move the scanning section along the axial direction with respect to the first housing frame and with respect to the second housing frame, to perform the telescopic motion.

21. The medical imaging apparatus of claim 19, further comprising an outer housing ring, the outer housing ring encompassing the scanning section and the first housing frame and extending in one axial direction at least to an outermost axial extension of the scanning section in the telescopic motion.

22. An arrangement, comprising:
the medical imaging apparatus of claim 18; and
a mobile stretcher for positioning a patient.

23. A vehicle, comprising the medical imaging apparatus of claim 18.

* * * * *